US012788767B2

(12) United States Patent
Checketts et al.

(10) Patent No.: US 12,788,767 B2
(45) Date of Patent: Nov. 10, 2026

(54) USE OF CANNABIDIOL IN THE TREATMENT OF SEIZURES ASSOCIATED WITH CHRNA4 MUTATION

(71) Applicant: Jazz Pharmaceuticals Research UK Limited, Sittingbourne (GB)

(72) Inventors: Daniel Adam Checketts, Sittingbourne (GB); Kevin James Craig, Sittingbourne (GB)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 794 days.

(21) Appl. No.: 18/005,868

(22) PCT Filed: Jul. 15, 2021

(86) PCT No.: PCT/EP2021/069884
§ 371 (c)(1),
(2) Date: Jan. 18, 2023

(87) PCT Pub. No.: WO2022/017949
PCT Pub. Date: Jan. 27, 2022

(65) Prior Publication Data

US 2023/0277560 A1 Sep. 7, 2023

(30) Foreign Application Priority Data

Jul. 20, 2020 (GB) ..................................... 2011168

(51) Int. Cl.
*A61K 31/00* (2006.01)
*A61K 31/4192* (2006.01)
*A61P 25/08* (2006.01)

(52) U.S. Cl.
CPC ........ *A61K 31/658* (2023.05); *A61K 31/4192* (2013.01); *A61P 25/08* (2018.01)

(58) Field of Classification Search
CPC ......... A61P 25/10; A61P 25/12; A61K 31/658
See application file for complete search history.

(56) References Cited

U.S. PATENT DOCUMENTS

| | | | |
|---|---|---|---|
| 8,632,825 | B2 | 1/2014 | Velasco Diez et al. |
| 8,790,719 | B2 | 7/2014 | Parolaro et al. |
| 9,017,737 | B2 | 4/2015 | Kikuchi et al. |
| 9,125,859 | B2 | 9/2015 | Whalley et al. |
| 9,474,726 | B2 | 10/2016 | Guy et al. |
| 9,675,654 | B2 | 6/2017 | Parolaro et al. |
| 9,949,936 | B2 | 4/2018 | Guy et al. |
| 9,949,937 | B2 | 4/2018 | Guy et al. |
| 9,956,183 | B2 | 5/2018 | Guy et al. |
| 9,956,184 | B2 | 5/2018 | Guy et al. |
| 9,956,185 | B2 | 5/2018 | Guy et al. |
| 9,956,186 | B2 | 5/2018 | Guy et al. |
| 9,962,341 | B2 | 5/2018 | Stott et al. |
| 10,039,724 | B2 | 8/2018 | Stott et al. |
| 10,092,525 | B2 | 10/2018 | Guy et al. |
| 10,098,867 | B2 | 10/2018 | Javid et al. |
| 10,111,840 | B2 | 10/2018 | Guy et al. |
| 10,137,095 | B2 | 11/2018 | Guy et al. |
| 10,220,005 | B2 | 3/2019 | Martinez-Orgado et al. |
| 10,226,433 | B2 | 3/2019 | Di Marzo et al. |
| 10,583,096 | B2 | 3/2020 | Guy et al. |
| 10,603,288 | B2 | 3/2020 | Guy et al. |
| 10,653,641 | B2 | 5/2020 | Robson et al. |
| 10,709,671 | B2 | 7/2020 | Guy et al. |
| 10,709,673 | B2 | 7/2020 | Guy |
| 10,709,674 | B2 | 7/2020 | Guy et al. |
| 10,729,665 | B2 | 8/2020 | Whalley et al. |
| 10,758,514 | B2 | 9/2020 | Liu et al. |
| 10,765,643 | B2 | 9/2020 | Guy et al. |
| 10,799,467 | B2 | 10/2020 | Whalley et al. |
| 10,807,777 | B2 | 10/2020 | Whittle |
| 10,849,860 | B2 | 12/2020 | Guy et al. |
| 10,918,608 | B2 | 2/2021 | Guy et al. |
| 10,966,939 | B2 | 4/2021 | Guy et al. |
| 11,000,486 | B2 | 5/2021 | Wright et al. |
| 11,065,209 | B2 | 7/2021 | Guy et al. |
| 11,065,227 | B2 | 7/2021 | Stott et al. |
| 11,096,905 | B2 | 8/2021 | Guy et al. |
| 11,147,776 | B2 | 10/2021 | Stott et al. |
| 11,147,783 | B2 | 10/2021 | Stott et al. |
| 11,154,516 | B2 | 10/2021 | Guy et al. |
| 11,154,517 | B2 | 10/2021 | Guy et al. |

(Continued)

FOREIGN PATENT DOCUMENTS

| | | |
|---|---|---|
| GB | 2531278 A | 4/2016 |
| GB | 2531282 A | 4/2016 |

(Continued)

OTHER PUBLICATIONS

Bertrand, D. et al., "How mutations in the nAChRs can cause ADNFLE epilepsy," Epilepsia, 43 Suppl 5:112-122 (2002); doi:10.1046/j.1528-1157.43.s.5.16.x.
Eadie, M. J., "Shortcomings in the current treatment of epilepsy," Expert Rev Neurother., 12(12):1419-1427 (2012).
Elsohly, M. & Gul, W., Handbook of Cannabis, Chapter 1, Constituents of Cannabis Sativa, Roger Pertwee, Ed., 2012, 21 pages.
EPIDIOLEX® (cannabidiol) oral solution, CV, Prescribing Information, 2018, 30 pages; https://www.accessdata.fda.gov/drugsatfda_docs/label/2018/210365lbl.pdf.
Kwan, P. et al., "Definition of drug resistant epilepsy: consensus proposal by the ad hoc Task Force of the ILAE Commission on Therapeutic Strategies," Epilepsia, 51(6):1069-1077; doi:10.1111/j.1528-1167.2009.02397.x. Epub Nov. 3, 2009. Erratum in: Epilepsia. Sep. 2010; 51(9):1922.

(Continued)

*Primary Examiner* — Sahar Javanmard
(74) *Attorney, Agent, or Firm* — COOLEY LLP

(57) ABSTRACT

The present invention relates to the use of cannabidiol (CBD) for the treatment of seizures associated with rare epilepsy syndromes. In particular the seizures associated with rare epilepsy syndromes that are treated are those which are experienced inpatients with CHRNA4 gene mutation. In a further embodiment the types of seizures include tonic-clonic, atonic, myoclonic and absence seizures. Preferably the dose of CBD is between 5 mg/kg/day to 50 mg/kg/day.

15 Claims, No Drawings

(56) References Cited

U.S. PATENT DOCUMENTS

| | | | |
|---|---|---|---|
| 11,160,757 | B1 | 11/2021 | Wilkhu et al. |
| 11,160,795 | B2 | 11/2021 | Guy et al. |
| 11,207,292 | B2 | 12/2021 | Guy et al. |
| 11,229,612 | B2 | 1/2022 | Wright et al. |
| 11,291,631 | B2 | 4/2022 | Shah |
| 11,311,498 | B2 | 4/2022 | Guy et al. |
| 11,318,109 | B2 | 5/2022 | Whalley et al. |
| 11,357,741 | B2 | 6/2022 | Guy et al. |
| 11,400,055 | B2 | 8/2022 | Guy et al. |
| 11,406,623 | B2 | 8/2022 | Guy et al. |
| 11,413,266 | B2 | 8/2022 | Biróet al. |
| 11,419,829 | B2 | 8/2022 | Whalley et al. |
| 11,426,362 | B2 | 8/2022 | Wright et al. |
| 11,446,258 | B2 | 9/2022 | Guy et al. |
| 11,590,087 | B2 | 2/2023 | Guy et al. |
| 11,633,369 | B2 | 4/2023 | Guy et al. |
| 11,679,087 | B2 | 6/2023 | Guy et al. |
| 11,684,598 | B2 | 6/2023 | Stott et al. |
| 11,701,330 | B2 | 7/2023 | Guy et al. |
| 11,766,411 | B2 | 9/2023 | Guy et al. |
| 11,793,770 | B2 | 10/2023 | Stott et al. |
| 11,806,319 | B2 | 11/2023 | Wilkhu et al. |
| 11,865,102 | B2 | 1/2024 | Guy et al. |
| 2015/0359756 | A1 | 12/2015 | Guy et al. |
| 2017/0239193 | A1 | 8/2017 | Guy et al. |
| 2018/0071210 | A1 | 3/2018 | Wilkhu et al. |
| 2018/0228751 | A1 | 8/2018 | Stott et al. |
| 2019/0167583 | A1 | 6/2019 | Shah |
| 2019/0314296 | A1 | 10/2019 | Wright et al. |
| 2019/0321307 | A1 | 10/2019 | Guy et al. |
| 2019/0365667 | A1 | 12/2019 | Wright et al. |
| 2020/0138738 | A1 | 5/2020 | Guy et al. |
| 2020/0179303 | A1 | 6/2020 | Guy et al. |
| 2020/0206153 | A1 | 7/2020 | Whalley et al. |
| 2020/0237683 | A1 | 7/2020 | Whalley et al. |
| 2020/0297656 | A1 | 9/2020 | Guy et al. |
| 2020/0352878 | A1 | 11/2020 | Guy et al. |
| 2021/0015789 | A1 | 1/2021 | Guy et al. |
| 2021/0052512 | A1 | 2/2021 | Guy et al. |
| 2021/0059949 | A1 | 3/2021 | Wilkhu et al. |
| 2021/0059960 | A1 | 3/2021 | Wilkhu et al. |
| 2021/0059976 | A1 | 3/2021 | Wilkhu et al. |
| 2021/0069333 | A1 | 3/2021 | Velasco Diez et al. |
| 2021/0100755 | A1 | 4/2021 | Whalley et al. |
| 2021/0169824 | A1 | 6/2021 | Guy et al. |
| 2021/0177773 | A1 | 6/2021 | Guy et al. |
| 2021/0290565 | A1 | 9/2021 | Guy et al. |
| 2021/0308072 | A1 | 10/2021 | Wright et al. |
| 2021/0330636 | A1 | 10/2021 | Guy et al. |
| 2021/0401771 | A1 | 12/2021 | Guy et al. |
| 2022/0000800 | A1 | 1/2022 | Guy et al. |
| 2022/0008355 | A1 | 1/2022 | Guy et al. |
| 2022/0016048 | A1 | 1/2022 | Guy et al. |
| 2022/0023232 | A1 | 1/2022 | Guy et al. |
| 2022/0040155 | A1 | 2/2022 | Guy et al. |
| 2022/0062197 | A1 | 3/2022 | Stott et al. |
| 2022/0062211 | A1 | 3/2022 | Stott et al. |
| 2022/0087951 | A1 | 3/2022 | Knappertz |
| 2022/0096397 | A1 | 3/2022 | Wright et al. |
| 2022/0168266 | A1 | 6/2022 | Guy et al. |
| 2022/0183997 | A1 | 6/2022 | Guy et al. |
| 2022/0184000 | A1 | 6/2022 | Guy et al. |
| 2022/0202738 | A1 | 6/2022 | Guy et al. |
| 2022/0211629 | A1 | 7/2022 | Wilkhu et al. |
| 2022/0226257 | A1 | 7/2022 | Guy et al. |
| 2022/0233495 | A1 | 7/2022 | Silcock et al. |
| 2022/0249396 | A1 | 8/2022 | Guy et al. |
| 2022/0257529 | A1 | 8/2022 | Guy et al. |
| 2022/0265573 | A1 | 8/2022 | Guy et al. |
| 2022/0288055 | A1 | 9/2022 | Silcock et al. |
| 2022/0378714 | A1 | 12/2022 | Guy et al. |
| 2022/0378715 | A1 | 12/2022 | Guy et al. |
| 2022/0378738 | A1 | 12/2022 | Guy et al. |
| 2022/0387347 | A1 | 12/2022 | Whalley et al. |
| 2022/0395470 | A1 | 12/2022 | Whalley et al. |
| 2022/0395471 | A1 | 12/2022 | Guy et al. |
| 2023/0000789 | A1 | 1/2023 | Guy et al. |
| 2023/0022487 | A1 | 1/2023 | Guy et al. |
| 2023/0024312 | A1 | 1/2023 | Whalley et al. |
| 2023/0026079 | A1 | 1/2023 | Guy et al. |
| 2023/0032502 | A1 | 2/2023 | Guy et al. |
| 2023/0038423 | A1 | 2/2023 | Silcock et al. |
| 2023/0068885 | A1 | 3/2023 | Guy et al. |
| 2023/0143812 | A1 | 5/2023 | Knappertz et al. |
| 2023/0235825 | A1 | 7/2023 | Thompson et al. |
| 2023/0248664 | A1 | 8/2023 | Guy |
| 2023/0263744 | A1 | 8/2023 | Guy |
| 2023/0277561 | A1 | 9/2023 | Checketts et al. |
| 2023/0277562 | A1 | 9/2023 | Checketts et al. |
| 2023/0277563 | A1 | 9/2023 | Checketts et al. |
| 2023/0285419 | A1 | 9/2023 | Checketts et al. |
| 2023/0285420 | A1 | 9/2023 | Checketts et al. |
| 2023/0285421 | A1 | 9/2023 | Checketts et al. |
| 2023/0285422 | A1 | 9/2023 | Checketts et al. |
| 2023/0285423 | A1 | 9/2023 | Checketts et al. |
| 2023/0285424 | A1 | 9/2023 | Checketts et al. |
| 2023/0285425 | A1 | 9/2023 | Checketts et al. |
| 2023/0285426 | A1 | 9/2023 | Checketts et al. |
| 2023/0285427 | A1 | 9/2023 | Checketts et al. |
| 2023/0285428 | A1 | 9/2023 | Checketts et al. |
| 2023/0301934 | A1 | 9/2023 | Whalley et al. |
| 2023/0301936 | A1 | 9/2023 | Guy |
| 2023/0310464 | A1 | 10/2023 | Checketts et al. |
| 2023/0372367 | A1 | 11/2023 | Checketts et al. |
| 2023/0372368 | A1 | 11/2023 | Checketts et al. |
| 2024/0016819 | A1 | 1/2024 | Craig |
| 2024/0025858 | A1 | 1/2024 | Silcock et al. |
| 2024/0033229 | A1 | 2/2024 | Guy et al. |
| 2024/0033272 | A1 | 2/2024 | Checketts et al. |
| 2024/0043388 | A1 | 2/2024 | Silcock et al. |
| 2024/0050452 | A1 | 2/2024 | Craig et al. |

FOREIGN PATENT DOCUMENTS

| | | | |
|---|---|---|---|
| GB | 2539472 | A | 12/2016 |
| WO | WO-2019207319 | A1 | 10/2019 |
| WO | WO-2020109806 | A1 | 6/2020 |

OTHER PUBLICATIONS

Laux, L. C. et al., "Long-term safety and efficacy of cannabidiol in children and adults with treatment resistant Lennox-Gastaut syndrome or Dravet syndrome: Expanded access program results," Epilepsy Research, 154:13-20 (2019).

Pertwee, R. G., "The Pharmacology and Therapeutic Potential of Cannabidiol," Cannabinoids, Chapter 3, DiMarzo, V. (Ed.), pp. 32-83 (2004).

Porter, B. E. & Jacobson, C., "Report of a parent survey of cannabidiol-enriched cannabis use in pediatric treatment-resistant epilepsy," Epilepsy Behav., 29(3):574-577 (2013).

Rodrguez-Tirado, C. S. et al., "Modulation of Nicotinic Receptors by Cannabinoids," The FASEB Journal, vol. 32, Issue S1, p. 533.78-533.78 (2018). Abstract.

Rosenberg, E. C. et al., "Quality of Life of Childhood Epilepsy (QOLCE) in pediatric patients enrolled in a prospective, open-label clinical study with cannabidiol (CBD)," Epilepsia, 58(8):e96-e100 (2017); doi:10.1111/epi.13815.

Sutor, B. & Zolles, G., "Neuronal nicotinic acetylcholine receptors and autosomal dominant nocturnal frontal lobe epilepsy: a critical review," Pflügers Arch—Eur J Physiol, 442:642-651 (2001); doi:10.1007/s004240100614.

Szaflarski, J. P. et al., "Long-term safety and treatment effects of cannabidiol in children and adults with treatment-resistant epilepsies: Expanded access program results," Epilepsia, 59:1540-1548 (2018).

Thurman, D. J. et al., "Standards for epidemiologic studies and surveillance of epilepsy," Epilepsia, 52 (Suppl 7):2-26 (2011).

Chiron, C. & Dulac, O., "The pharmacologic treatment of Dravet syndrome," Epilepsia, 52(Suppl 2):72-5 (Apr. 2011).

(56) References Cited

OTHER PUBLICATIONS

Dulac, O. & Kaminska, A., “Use of Lamotrigine in Lennox-Gastaut and Related Epilepsy Syndromes,” J. Child Neurolog., 12(Suppl 1):S23-S29 (Nov. 1997).
Kelley, S. A. & Kossoff, E. H., “Doose syndrome (myoclonic-astatic epilepsy): 40 years of progress,” Developmental Med. & Child Neurol., 52(11):988-93 (Nov. 2010).
Lutz, B. et al., “On-demand activation of the endocannabinoid system in the control of neuronal excitability and epileptiform seizures,” Biochemical Pharmacology 68:1691-1698 (Nov. 2004).
Mayo Clinic, “Carbamazepine (oral route),” [drug information], provided by Merative, Micromedex®, DRG-20062739, (initial publication date unknown; last updated Feb. 1, 2026). [Retrieved from the Internet on Feb. 12, 2026; at URL: https://www.mayoclinic.org/drugs-supplements/carbamazepine-oral-route/description/drg-20062739], 28 pages.
Mayo Clinic, “Phenytoin (oral route),” [drug information], provided by Merative, Micromedex®, DRG-20072875, (initial publication date unknown; last updated Feb. 1, 2026). [Retrieved from the Internet on Feb. 12, 2026; at URL: https://www.mayoclinic.org/drugs-supplements/phenytoin-oral-route/description/drg-20072875, 24 pages.
Mayo Clinic, “Vigabatrin (oral route),” [drug information], provided by Merative, Micromedex®, DRG-20066675, (initial publication date unknown, last updated Feb. 1, 2026). [Retrieved from the Internet on Mar. 2, 2026; at URL: https://www.mayoclinic.org/drugs-supplements/vigabatrin-oral-route/description/drg-20066675], 19 pages.
Scheffer, I. E. et al., “Autosomal dominant nocturnal frontal lobe epilepsy. A distinctive clinical disorder,” Brain, 118(Pt 1):61-73 (Feb. 1995). doi: 10.1093/brain/118.1.61.
U.S. Food and Drug Administration, “What We Do,” [website] FDA.gov., U.S. Department of Health and Human Services, (initial publication date unknown; last updated Nov. 21, 2023). [Retrieved from the Internet on Feb. 12, 2026, at URL: https://www.fda.gov/about-fda/what-we-do], 5 pages.
Vossler, D. G. & Gidal, B. E., “A summary of antiseizure medications available in the United States: 4th Edition,” American Epilepsy Society, (Revised Apr. 1, 2024), 28 pages.

USE OF CANNABIDIOL IN THE TREATMENT OF SEIZURES ASSOCIATED WITH CHRNA4 MUTATION

CROSS-REFERENCE TO RELATED APPLICATIONS

This application is a U.S. National Phase application, filed under 35 U.S.C. § 371 (c), of International Application No. PCT/EP2021/069884, filed Jul. 15, 2021, which claims priority to, and the benefit of, United Kingdom Patent Application No. 2011168.8, filed Jul. 20, 2020. Each of these documents is incorporated by reference herein in its entirety for all purposes.

FIELD OF THE INVENTION

The present invention relates to the use of cannabidiol (CBD) for the treatment of seizures associated with rare epilepsy syndromes. In particular the seizures associated with rare epilepsy syndromes that are treated are those which are experienced in patients with CHRNA4 gene mutation. In a further embodiment the types of seizures include tonic-clonic, atonic, myoclonic and absence seizures. Preferably the dose of CBD is between 5 mg/kg/day to 50 mg/kg/day.

In a further embodiment the CBD used is in the form of a highly purified extract of cannabis such that the CBD is present at greater than 95% of the total extract (w/w) and the cannabinoid tetrahydrocannabinol (THC) has been substantially removed, to a level of not more than 0.15% (w/w).

Preferably the CBD used is in the form of a botanically derived purified CBD which comprises greater than or equal to 98% (w/w) CBD and less than or equal to 2% (w/w) of other cannabinoids. More preferably the other cannabinoids present are THC at a concentration of less than or equal to 0.1% (w/w); CBD-C1 at a concentration of less than or equal to 0.15% (w/w); CBDV at a concentration of less than or equal to 0.8% (w/w); and CBD-C4 at a concentration of less than or equal to 0.4% (w/w). The botanically derived purified CBD preferably also comprises a mixture of both trans-THC and cis-THC. Alternatively, a synthetically produced CBD is used.

Most preferably the other cannabinoids present are THC at a concentration of about 0.01% to about 0.1% (w/w); CBD-C1 at a concentration of about 0.1% to about 0.15% (w/w); CBDV at a concentration of about 0.2% to about 0.8% (w/w); and CBD-C4 at a concentration of about 0.3% to about 0.4% (w/w). Most preferably still the THC is present at a concentration of about 0.02% to about 0.05% (w/w).

Where the CBD is given concomitantly with one or more other anti-epileptic drugs (AED), the CBD may be formulated for administration separately, sequentially or simultaneously with one or more AED or the combination may be provided in a single dosage form.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from intractable or "treatment-resistant epilepsy" (TRE).

Intractable or treatment-resistant epilepsy was defined in 2009 by the International League Against Epilepsy (ILAE) as "failure of adequate trials of two tolerated and appropriately chosen and used AED schedules (whether as monotherapies or in combination) to achieve sustained seizure freedom" (Kwan et al., 2009).

Individuals who develop epilepsy during the first few years of life are often difficult to treat and as such are often termed treatment resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from an investigation into the type of seizures that the patient is experiencing is undertaken. Clinical observations and electroencephalography (EEG) tests are conducted and the type(s) of seizures are classified according to the ILEA classification.

Generalized seizures, where the seizure arises within and rapidly engages bilaterally distributed networks, can be split into six subtypes: tonic-clonic (grand mal) seizures; absence (petit mal) seizures; clonic seizures; tonic seizures; atonic seizures and myoclonic seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a bilateral convulsive seizure, which is the proposed terminology to replace secondary generalized seizures (generalized seizures that have evolved from focal seizures and are no longer remain localized).

Focal seizures where the subject's awareness/responsiveness is altered are referred to as focal seizures with impairment and focal seizures where the awareness or responsiveness of the subject is not impaired are referred to as focal seizures without impairment.

The CHRNA4 gene encodes the α4 subunit of a larger protein called a neuronal nicotinic acetylcholine receptor (nAChR), which is made up of a combination of five subunits. nAChR proteins are widely distributed in the brain and act as channels which open in response to chemicals such as acetylcholine and nicotine. Thus, they play an important role in the neuron signaling. nAChR channels affect a wide range of brain functions, including sleep and arousal, fatigue, anxiety, attention, pain perception, and memory. The channels are also active before birth, suggesting they are involved in early brain development.

Mutations in the CHRNA4 gene have been identified in people with autosomal dominant nocturnal frontal lobe epilepsy (ADNFLE).

Autosomal dominant nocturnal frontal lobe epilepsy (ADNFLE) is an uncommon, inherited form of epilepsy characterized by seizures occurring at night during sleep. Some people with ADNFLE also have seizures during the day. These seizures can last from a few seconds to a few minutes, and can vary from causing simple arousal from sleep, to dramatic muscle spasms and movements.

Most people with ADNFLE have normal intellect, but some affected people have reduced intellect. Some people with ADNFLE also have psychiatric disorders or behavior problems, but it is unclear if these are directly related to ADNFLE. The condition is inherited in an autosomal dominant manner and may be caused by a mutation in any of several genes.

The onset of ADNFLE ranges from infancy to adulthood, but most cases begin in childhood and episodes tend to become milder and less frequent with age.

Treatment of ADNFLE involves anti-seizure medications to control seizures. Carbamazepine is usually used as the main drug but oxcarbamazepine, topiramate and acetazolamide may also be used as add-on therapies.

Cannabidiol (CBD), a non-psychoactive derivative from the cannabis plant, has demonstrated anti-convulsant properties in several anecdotal reports, pre-clinical and clinical studies both in animal models and humans. Three randomized control trials showed efficacy of the purified pharmaceutical formulation of CBD in patients with Dravet and Lennox-Gastaut syndrome.

Based on these three trials, a botanically derived purified CBD preparation was approved by FDA in June 2018 for the treatment of seizures associated with Dravet and Lennox-Gastaut syndromes.

Documents including WO2020/109806, GB2531282 and GB2531278 disclose the effectiveness of highly purified CBD in the treatment of seizures associated with epileptic syndromes such as Lennox-Gastaut Syndrome. However, there is no data of patients with CHRNA4-related epilepsy nor is there any mention of this condition.

The applicant has found by way of an open label, expanded-access program that treatment with CBD resulted in a significant reduction in tonic-clonic, atonic, myoclonic and absence seizures in patients with CHRNA4 mutation.

BRIEF SUMMARY OF THE DISCLOSURE

In accordance with a first aspect of the present invention there is provided a cannabidiol (CBD) preparation for use in the treatment of seizures associated with CHRNA4 mutation.

In a further embodiment, the seizures associated with CHRNA4 mutation are tonic-clonic, atonic, myoclonic and absence seizures.

In a further embodiment, the CBD preparation comprises greater than 95% (w/w) CBD and not more than 0.15% (w/w) tetrahydrocannabinol (THC).

Preferably the CBD preparation comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC.

Preferably the CBD preparation is used in combination with one or more concomitant anti-epileptic drugs (AED).

Preferably the one or more AED is rufinamide.

In one embodiment the CBD is present is isolated from cannabis plant material. Preferably at least a portion of at least one of the cannabinoids present in the CBD preparation is isolated from cannabis plant material.

In a further embodiment the CBD is present as a synthetic preparation. Preferably at least a portion of at least one of the cannabinoids present in the CBD preparation is prepared synthetically.

Preferably the dose of CBD is greater than 5 mg/kg/day. More preferably the dose of CBD is 20 mg/kg/day. More preferably the dose of CBD is 25 mg/kg/day. More preferably the dose of CBD is 50 mg/kg/day.

In accordance with a second aspect of the present invention there is provided a method of treating seizures associated with CHRNA4 mutation comprising administering a cannabidiol (CBD) preparation to the subject in need thereof.

Definitions

Definitions of some of the terms used to describe the invention are detailed below:

Over 100 different cannabinoids have been identified, see for example, Handbook of Cannabis, Roger Pertwee, Chapter 1, pages 3 to 15. These cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Highly purified cannabinoids" are defined as cannabinoids that have been extracted from the cannabis plant and purified to the extent that other cannabinoids and non-cannabinoid components that are co-extracted with the cannabinoids have been removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example, it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Tonic-clonic seizures" consist of two phases: the tonic phase and the clonic phase. In the tonic phase the body becomes entire rigid, and in the clonic phase there is uncontrolled jerking. Tonic-clonic seizures may or may not be preceded by an aura, and are often followed by headache, confusion, and sleep. They may last mere seconds or continue for several minutes. These seizures are also known as a grand mal seizure.

"Atonic seizures" occur when a person suddenly loses muscle tone so their head or body may go limp. They are also known as drop attacks. In some children, only their head drops suddenly. They can begin in one area or side of the brain (focal onset) or both sides of the brain (generalized onset).

"Myoclonic seizures" are characterised by a 'muscle jerk'. Myoclonic seizures are brief but can happen in clusters (many happening close together in time) and often happen shortly after waking. In myoclonic seizures the person is conscious, but they are classified as generalised seizures.

"Absence seizures" also may be called "petit mal" seizures. These types of seizure cause a loss of awareness for a short time. They mainly affect children although can happen at any age. During an absence seizure, a person may: stare blankly into space; look like they're "daydreaming"; flutter their eyes; make slight jerking movements of their body or limbs. The seizures usually only last up to 15 seconds and may occur several times a day.

DETAILED DESCRIPTION

Preparation of Highly Purified CBD Extract

The following describes the production of the highly-purified (>95% w/w) cannabidiol extract which has a known and constant composition.

In summary the drug substance used is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD. Although the CBD is highly purified because it is produced from a cannabis plant rather than synthetically there is a small number of other cannabinoids which are co-produced and co-extracted with the CBD. Details of these cannabinoids and the quantities in which they are present in the medication are as described in Table A below.

TABLE A

Composition of highly purified CBD extract

| Cannabinoid | Concentration |
|---|---|
| CBD | >95% w/w |
| CBDA | NMT 0.15% w/w |
| CBDV | NMT 1.0% w/w |
| $\Delta^9$ THC | NMT 0.15% w/w |
| CBD-C4 | NMT 0.5% w/w |

>—greater than
NMT—not more than

Preparation of Botanically Derived Purified CBD

The following describes the production of the botanically derived purified CBD which comprises greater than or equal to 98% w/w CBD and less than or equal to other cannabinoids was used in the open label, expanded-access program described in Example 1 below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD w/w, typically greater than 98% w/w.

The *Cannabis sativa* L. plants are grown, harvested, and processed to produce a botanical extract (intermediate) and then purified by crystallization to yield the CBD (botanically derived purified CBD).

The plant starting material is referred to as Botanical Raw Material (BRM); the botanical extract is the intermediate; and the active pharmaceutical ingredient (API) is CBD, the drug substance.

All parts of the process are controlled by specifications. The botanical raw material specification is described in Table B and the CBD API is described in Table C.

TABLE B

CBD botanical raw material specification

| Test | Method | Specification |
|---|---|---|
| Identification: | | |
| A | Visual | Complies |
| B | TLC | Corresponds to standard (for CBD & CBDA) |
| C | HPLC/UV | Positive for CBDA |
| Assay: CBDA + CBD | In-house (HPLC/UV) | NLT 90% of assayed cannabinoids by peak area |
| Loss on Drying | Ph. Eur. | NMT 15% |
| Aflatoxin | UKAS method | NMT 4 ppb |
| Microbial: | | |
| TVC | Ph. Eur. | NMT$10^7$ cfu/g |
| Fungi | | NMT$10^5$ cfu/g |
| *E. coli* | | NMT$10^2$ cfu/g |
| Foreign Matter: | Ph. Eur. | NMT 2% |
| Residual Herbicides and Pesticides | Ph. Eur. | Complies |

TABLE C

Specification of an exemplary botanically derived purified CBD preparation

| Test | Test Method | Limits |
|---|---|---|
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0% |
| CBDA | HPLC-UV | NMT 0.15% w/w |
| CBDV | | 0.2-1.0% w/w |

TABLE C-continued

Specification of an exemplary botanically derived purified CBD preparation

| Test | Test Method | Limits |
|---|---|---|
| THC | | 0.01-0.1% w/w |
| CBD-C4 | | 0.3-0.5% w/w |
| Residual Solvents: | | |
| Alkane | GC | NMT 0.5% w/w |
| Ethanol | | NMT 0.5% w/w |
| Residual Water | Karl Fischer | NMT 1.0% w/w |

The purity of the botanically derived purified CBD preparation was greater than or equal to 98%. The botanically derived purified CBD includes THC and other cannabinoids, e.g., CBDA, CBDV, CBD-C1, and CBD-C4.

In some embodiments, the CBD preparation comprises not more than 0.15% THC based on total amount of cannabinoid in the preparation. In some embodiments, the CBD preparation comprises about 0.01% to about 0.1% THC based on total amount of cannabinoid in the preparation. In some embodiments, the CBD preparation comprises about 0.02% to about 0.05% THC based on total amount of cannabinoid in the preparation.

In some embodiments, the CBD preparation comprises about 0.2% to about 1.0% CBDV based on total amount of cannabinoid in the preparation. In some embodiments, the CBD preparation comprises about 0.2% to about 0.8% CBDV based on total amount of cannabinoid in the preparation.

In some embodiments, the CBD preparation comprises about 0.3% to about 0.5% CBD-C4 based on total amount of cannabinoid in the preparation. In some embodiments, the CBD preparation comprises about 0.3% to about 0.4% CBD-C4 based on total amount of cannabinoid in the preparation.

In some embodiments, the CBD preparation comprises about 0.1% to about 0.15% CBD-C1 based on total amount of cannabinoid in the preparation.

Distinct chemotypes of the *Cannabis sativa* L. plant have been produced to maximize the output of the specific chemical constituents, the cannabinoids. Certain chemovars produce predominantly CBD. Only the (−)-trans isomer of CBD is believed to occur naturally. During purification, the stereochemistry of CBD is not affected.

Production of CBD Botanical Drug Substance

An overview of the steps to produce a botanical extract, the intermediate, are as follows:

a) Growing
b) Direct drying
c) Decarboxylation
d) Extraction—using liquid $CO_2$
e) Winterization using ethanol
f) Filtration
g) Evaporation High CBD chemovars were grown, harvested, dried, baled and stored in a dry room until required. The botanical raw material (BRM) was finely chopped using an Apex mill fitted with a 1 mm screen. The milled BRM was stored in a freezer prior to extraction.

Decarboxylation of CBDA to CBD was carried out using heat. BRM was decarboxylated at 115° C. for 60 minutes.

Extraction was performed using liquid $CO_2$ to produce botanical drug substance (BDS), which was then crystalized to produce the test material. The crude CBD BDS was winterized to refine the extract under standard conditions (2 volumes of ethanol at −20° C. for approximately 50 hours). The precipitated waxes were removed by filtration and the solvent was removed to yield the BDS.

Production of Botanically Derived Purified CBD Preparation

The manufacturing steps to produce the botanically derived purified CBD preparation from BDS were as follows:

a) Crystallization using $C_5$-$C_{12}$ straight chain or branched alkane
b) Filtration
c) Vacuum drying The BDS produced using the methodology above was dispersed in $C_5$-$C_{12}$ straight chain or branched alkane. The mixture was manually agitated to break up any lumps and the sealed container then placed in a freezer for approximately 48 hours. The crystals were isolated via vacuum filtration, washed with aliquots of cold $C_5$-$C_{12}$ straight chain or branched alkane, and dried under a vacuum of <10 mb at a temperature of 60° C. until dry. The botanically derived purified CBD preparation was stored in a freezer at −20° C. in a pharmaceutical grade stainless steel container, with FDA food grade approved silicone seal and clamps.

Physicochemical Properties of the Botanically Derived Purified CBD

The botanically derived purified CBD used in the clinical trial described in the invention comprises greater than or equal to 98% (w/w) CBD and less than or equal to 2% (w/w) of other cannabinoids. The other cannabinoids present are THC at a concentration of less than or equal to 0.1% (w/w); CBD-C1 at a concentration of less than or equal to 0.15% (w/w); CBDV at a concentration of less than or equal to 0.8% (w/w); and CBD-C4 at a concentration of less than or equal to 0.4% (w/w).

The botanically derived purified CBD used additionally comprises a mixture of both trans-THC and cis-THC. It was found that the ratio of the trans-THC to cis-THC is altered and can be controlled by the processing and purification process, ranging from 3.3:1 (trans-THC:cis-THC) in its unrefined decarboxylated state to 0.8:1 (trans-THC:cis-THC) when highly purified.

Furthermore, the cis-THC found in botanically derived purified CBD is present as a mixture of both the (+)-cis-THC and the (−)-cis-THC isoforms.

Clearly a CBD preparation could be produced synthetically by producing a composition with duplicate components.

Example 1 below describes the use of a botanically derived purified CBD in an open label, expanded-access program to investigate the clinical efficacy and safety of purified pharmaceutical cannabidiol formulation (CBD) in the treatment of seizures associated with CHRNA4 mutation.

Example 1: Clinical Efficacy and Safety of Purified Pharmaceutical Cannabidiol (CBD) in the Treatment of Patients Diagnosed with CHRNA4 Mutation Study Design The subject was required to be on one or more AEDs at stable doses for a minimum of two weeks prior to baseline and to have stable vagus nerve stimulation (VNS) settings and ketogenic diet ratios for a minimum of four weeks prior to baseline.

The patient was administered botanically derived purified CBD in a 100 mg/mL sesame oil-based solution. Dose was increased to a goal of 25 mg/kg/day.

A maximum dose of 50 mg/kg/day could be utilised for the patient if they were tolerating the medication but had not achieved seizure control; the patient had further weekly titration by 5 mg/kg/day.

There was one patient in this study, and they received CBD for 24 weeks. Modifications were made to concomitant AEDs as per clinical indication.

Seizure frequency, intensity, and duration were recorded by caregivers in a diary during a baseline period of at least 28 days. Changes in seizure frequency relative to baseline were calculated after at least 2 weeks and at defined time-points of treatment.

Statistical Methods:

Patients may be defined as responders if they had more than 50% reduction in seizure frequency compared to baseline. The percent change in seizure frequency was calculated as follows:

$$\%\ \text{change seizure frequency} = \frac{((\text{weekly seizure frequency time interval}) - (\text{weekly seizure frequency Baseline}))}{(\text{weekly seizure frequency Baseline})} \times 100$$

The percent change of seizure frequency may be calculated for any time interval where seizure number has been recorded. For the purpose of this example the percent change of seizure frequency for the end of the treatment period was calculated as follows:

$$\%\ \text{reduction seizure frequency} = \frac{((\text{weekly seizure frequency Baseline}) - (\text{weekly seizure frequency End}))}{(\text{weekly seizure frequency Baseline})} \times 100$$

Results

Patient Description

One patient enrolled in the open label, expanded-access program had CHRNA4 mutation. The patient experienced several different seizure types including tonic-clonic, atonic, myoclonic and absence seizures and was taking one concomitant AED.

The patient was 7 years old and he was male as detailed in Table 1 below.

TABLE 1

Patient demographics, seizure type and concomitant medication

| Patient Number | Age (years) | Sex | Seizure types | Concomitant AEDs |
|---|---|---|---|---|
| 1 | 7.45 | M | Tonic-clonic, atonic, myoclonic, absence | RFN |

RFN=rufinamide

Study Medication and Concomitant Medications

The patient on the study was titrated up to 25 mg/kg/day of CBD.

The patient was on one concomitant AED at the time of starting CBD.

Clinical Changes

Table 2 illustrates the seizure frequency for the patient as well as the dose of CBD given.

TABLE 2

Seizure frequency data for Patient 1

| Patient 1 | Seizure Type | | | | |
|---|---|---|---|---|---|
| Time | Tonic-clonic | Atonic | Myoclonic | Absence | Dose CBD (mg/kg/day) |
| Baseline | 0.4 | 2800.0 | 2800.0 | 0.0 | — |
| 4 weeks | 1.0 | 2800.0 | 2800.0 | 0.0 | 15.0 |
| 8 weeks | 0.0 | 2800.0 | 2800.0 | 0.0 | 25.0 |
| 12 weeks | 1.0 | 2561.0 | 2560.0 | 0.0 | 25.0 |
| 16 weeks | 3.0 | 1260.0 | 840.0 | 84.0 | 25.0 |
| 24 weeks | 18.7 | 840.0 | 840.0 | 140.0 | 23.8 |

Patient 1 was treated for 24 weeks and experienced a 70% reduction in atonic and myoclonic seizures over the treatment period.

Overall, CBD was effective in reducing the frequency of atonic and myoclonic seizures.

CONCLUSIONS

These data indicate that CBD was able to significantly reduce the number of seizures associated with CHRNA4 mutation. Clearly the treatment is of significant benefit in this difficult to treat epilepsy syndrome given the high response rate experienced in the patient.

In conclusion, this study signifies the use of CBD for treatment of seizures associated with CHRNA4 mutation. Seizure types include atonic and myoclonic seizures for which seizure frequency rates decreased by significant rates, by 70%.

The invention claimed is:

1. A method of treating seizures associated with a CHRNA4 mutation, the method comprising administering a cannabidiol (CBD) drug substance to a subject in need thereof, wherein the CBD drug substance comprises greater than 95% (w/w) CBD, and wherein administration of the CBD drug substance provides a dose of CBD in the range of about 5 mg/kg/day to about 50 mg/kg/day.

2. The method of claim 1, wherein the seizures associated with CHRNA4 mutation are tonic-clonic, atonic, myoclonic and absence seizures.

3. The method of claim 1, wherein the CBD drug substance comprises greater than 95% (w/w) CBD and not more than 0.15% (w/w) tetrahydrocannabinol (THC).

4. The method of claim 1, wherein the CBD drug substance comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC.

5. The method of claim 1, wherein the CBD drug substance is used in combination with one or more concomitant anti-epileptic drugs (AED).

6. The method of claim 5, wherein the one or more AED is rufinamide.

7. The method of claim 1, wherein the CBD is isolated from *Cannabis* plant material.

8. The method of claim 1 wherein the CBD drug substance comprises at least one cannabinoid in addition to CBD, and at least a portion of at least one of the non-CBD cannabinoids present in the CBD drug substance is isolated from *Cannabis* plant material.

9. The method of claim 1, wherein the CBD is present as a synthetic preparation.

10. The method of claim 9, wherein the CBD drug substance comprises at least one cannabinoid in addition to CBD, and at least a portion of at least one of the non-CBD cannabinoids present in the CBD drug substance is prepared synthetically.

11. The method of claim 1, wherein the dose of CBD than in the range of 5 mg/kg/day to 25 mg/kg/day.

12. The method of claim 1, wherein the dose of CBD is 20 mg/kg/day.

13. The method of claim 1, wherein the dose of CBD is 25 mg/kg/day.

14. The method of claim 1, wherein the dose of CBD is 50 mg/kg/day.

15. The method of claim 1, wherein the dose of CBD is in the range of 10 mg/kg/day to 25 mg/kg/day.

* * * * *